United States Patent [19]

Wat

[11] 4,055,412
[45] Oct. 25, 1977

[54] PHENYLUREIDOIMIDAZOLIDINEDIONES AS PLANT PROTECTANTS

[75] Inventor: Edward Koon Wah Wat, Wilmington, Del.

[73] Assignee: E. I. Du Pont de Nemours and Company, Wilmington, Del.

[21] Appl. No.: 643,392

[22] Filed: Dec. 22, 1975

[51] Int. Cl.$^2$ ............................................. A01N 9/22
[52] U.S. Cl. ...................................................... 71/92
[58] Field of Search ............................. 71/92; 424/273

[56] References Cited

U.S. PATENT DOCUMENTS

| 2,723,274 | 11/1955 | Kaiser et al. | 71/92 |
| 3,305,557 | 2/1967 | Lubowe | 424/273 |
| 3,443,925 | 5/1969 | Kitasaki et al. | 71/92 |
| 3,818,032 | 6/1974 | Moser et al. | 71/92 |
| 3,830,908 | 8/1974 | Klippel et al. | 424/273 |

OTHER PUBLICATIONS

Baskakov et al., "Hydantoin Herbicides" (1972) CA 77 No. 110,578s (1972).
Patton, "Reactions of Isocyanates With etc.," (1966) J. Org. Chem. 32 pp. 383–388 (1967).
Sprankle et al., "Rapid Inactivation etc," (1975) Weed Sci. 23 pp. 224–228 (1975).

Primary Examiner—Glennon H. Hollrah

[57] ABSTRACT

Urea compounds of the formula:

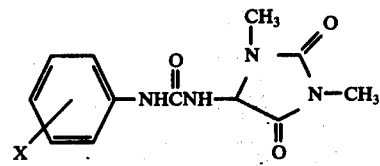

wherein X is hydrogen, fluorine, methoxy, meta-chlorine or meta-bromine, are useful for protecting plants from atmospheric ozone damage.

6 Claims, No Drawings

PHENYLUREIDOIMIDAZOLIDINEDIONES AS PLANT PROTECTANTS

BACKGROUND OF THE INVENTION

Synthesis of two phenylureidoimidazolidinediones of the formula:

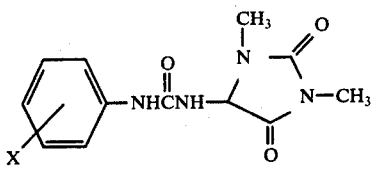

X = H and m-Cl, is taught in J. Org. Chem., 32, 383 (1967). No utility is disclosed.

Ozone is a common air pollutant, especially near urban areas and has been found to damage crop plants, ornamental plants and shade and forest trees.

Imidazolidone-ureas such as

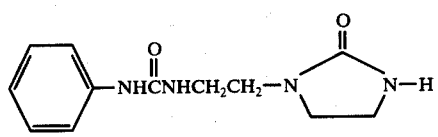

were disclosed in U.S. Pat. No. 3,859,301 to be useful in protecting plants against atmospheric ozone.

SUMMARY OF THE INVENTION

This invention encompasses a method of preventing ozone damage to plants. The method consists essentially of applying an effective amount of a compound of Formula I:

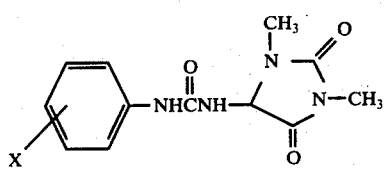

(I)

wherein X is selected from hydrogen, fluorine, methoxy, meta-chlorine, or meta-bromine.

The invention also encompasses compositions consisting essentially of an effective amount of the above compound and at least one of (a) an inert diluent or (b) a surfactant.

Application can be made to the foliage or the soil of the plants to be protected.

DETAILED DESCRIPTION OF THE INVENTION

Preferred for their higher protective ability are the compounds of Formula I where X is hydrogen, fluorine, or para-methoxy.

Specifically preferred for their superior activity are:

1. 1,3-Dimethyl-4-phenylureido-2,5-imidazolidinedione, m.p. 188°-189° C.
2. 1,3-Dimethyl-4-(4-fluorophenylureido)-2,5-imidazolidinedione, m.p. 98° C.
3. 1,3-Dimethyl-4-(2-fluorophenylureido)-2,5-imidazolidinedione, m.p. 103.5° C.
4. 1,3-Dimethyl-4-(4-methoxyphenylureido)-2,5-imidazolidinedione, m.p. 115°-119° C.

The phenylureidoimidazolidinediones of this invention can be prepared by reacting 4-amino-1,3-dimethyl-2,5-imidazolidinedione [J. Org. Chem., 32, 383 (1967)] with the appropriately substituted phenyl isocyanate in an inert solvent such as methylene chloride or benzene.

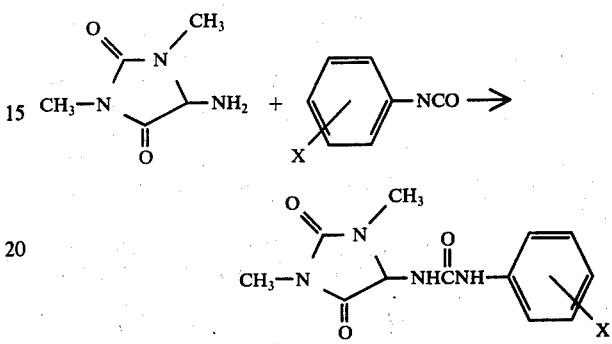

Synthesis of 1,3-Dimethyl-4-phenylureido-2,5-imidazolidinedione

To a stirred solution of 11 parts of 4-amino-1,3-dimethyl-2,5-imidazolidinedione in 200 parts of methylene chloride at ambient temperature is added dropwise a solution of 9 parts of phenyl isocyanate in 60 parts of methylene chloride. After stirring for 4 hours, the precipitated product is collected by filtration and recrystallized from a mixture of benzene and hexane to give 18 parts of pure material, m.p. 188°-189° C.

The following compounds can also be prepared as in the synthesis above by using the appropriately substituted phenyl isocyanate:

1,3-Dimethyl-4-(4-fluorophenylureido)-2,5-imidazolidinedione, m.p. 98° C.
1,3-Dimethyl-4-(2-fluorophenylureido)-2,5-imidazolidinedione, m.p. 103.5° C.
1,3-Dimethyl-4-(3-bromophenylureido)-2,5-imidazolidinedione
1,3-Dimethyl-4-(3-chlorophenylureido)-2,5-imidazolidinedione, m.p. 173°-182° C.
1,3Dimethyl-4-(4-methoxphenylureido)-2,5-imidazolidinedione, m.p. 115°-119° C.

Formulation of the Compounds

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulations. The formulations, broadly, contain about 1 to 99% by weight of active ingredient(s) and at least one of a) about 0.1 to 20% surfactant(s) and b) about 5 to 99% solid or liquid diluent(s). More specifically, they will contain these ingredients in the following approximate proportions:

|  | Percent by weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," Second Edn., Dorland Books, Cadwel, N.J. The more absorptive diluents are preferred for wettable powders and the denser ones for dusts. Typical liquid diluents and solvents are described in Marsden, "Solvents Guide," Second Edn., Interscience, New York, 1950. Solubility under 0.1% is preferred for suspension concentrates; solution concentrates are preferably stable against phase separation of 0° C. "McCutcheon's Detergents and Emulsifiers Annual," Allured Publ. Corp., Ridgewood N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon performed granular carriers or by agglomeration techniques. See J. E. Browning, "Agglomeration," Chemical Engineering, Dec. 4, 1967, pp. 147ff. and "Perry's Chemical Engineer's Handbook," Fourth Edn., McGraw-Hill, N.Y., 1963, pp. 8–59ff.

For further information regarding the art of formulation, see for example:
- J. B. Buchanan, U.S. Pat. No. 3,576,834, Apr. 27, 1971, Col. 5 Line 36 through Col. 7 Line 70 and Ex. 1–4, 106, 123–140.
- R. R. Shaffer, U.S. Pat. No. 3,560,616, Feb. 2, 1971, Col. 3 Line 48 through Col. 7 Line 26 and Examples 3–9, 11–18.
- E. Somers, "Formulation," Chapter 6 in Torgeson, "Fungicides", Vol. I, Academic Press, New York, 1967.

EXAMPLE I

Wettable Powder

| 1,3-dimethyl-4-phenylureido-2,5-imidazolidinedione | 40% |
| --- | --- |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S.N. 50 sieve (0.3 mm opening) before packaging.

All compounds of the invention may be formulated in the same manner.

EXAMPLE II

Wettable Powder

| 1,3-dimethyl-4-(4-methoxyphenylureido)-2,5-imidazolidinedione | 50% |
| --- | --- |
| sodium alkylnaphthalenesulfonate | 2% |
| low viscosity methyl cellulose | 2% |
| diatomaceous earth | 46% |

The ingredients are blended, coarsely hammermilled and then air milled to produce particles of active essentially all below 10 microns in diameter. The product is reblended before packaging.

EXAMPLE III

Granule

| wettable powder of Example II | 15% |
| --- | --- |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S.N. 18 to 40 sieves), the granules are removed, dried, and screened. Oversize material is crushed to produce additional material in the desired range. These granules contain 7.5% active ingredient.

EXAMPLE IV

Aqueous Suspension

| 1,3-dimethyl-4-(4-fluorophenylureido)-2,5-imidazolidinedione | 25% |
| --- | --- |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE V

Solution

| 1,3-dimethyl-4-(2-fluorophenylureido)-2,5-imidazolidinedione | 30% |
| --- | --- |
| dimethylformamide | 70% |

The ingredients are combined and stirred to produce a solution, which can be used for low volume applications.

Use of the Compounds

The compounds of the invention are useful to protect plants against the harmful effects of ozone. The amount of compound required for optimum effects will depend on the particular crop and environment under which it is growing. Within the meaning of this case, the amount of compound necessary to accomplish protection against ozone will be termed an "effective amount." Normally, the rate at which the compound is applied will range from 0.02 to 3.0 kilograms per hectare although higher rates can be used. One skilled in the art will be able to select the appropriate rate of application for any particular situation. Plants that can be protected from the deleterious effects of ozone include oranges, lemons, tobacco, grapes, potatoes, tomatoes, soybeans, corn, lettuce, alfalfa and ornamental plants.

The compounds of the present invention can be used in the form of compositions which are prepared by admixing at least one of the active compounds with an inert diluent, such as pest control adjuvant or modifiers, to provide compositions in the form of dusts, water-dispersible powders, high-strength concentrates, and aqueous or organic dispersions. Thus, the compounds of this invention can be used with a carrier or diluent agent such as a finely divided solid, an organic liquid, water, a wetting agent, a dispersing agent, an emulsifying agent, or any suitable combination of these.

The compositions, especially liquids and wettable powders, may contain as a conditioning agent one or more surface-active agents, sometimes called surfactants, in amounts sufficient to render a given composition containing the compounds of this invention readily dispersible in water or in oil.

EXAMPLE VI

Pinto beans (*Phaseolus vulgaris*) were grown in vermiculite in 4-inch plastic pots under 12-hour days with 2200-foot candles illumination (fluorescent plus incandescent). The daytime temperature and relative humidity were 24° C. and 75%, respectively. At night they were 18° C and 85%. Thirteen days after planting a representative plant was sprayed with a 500 ppm solution of 1,3-dimethyl-4-phenylureido-2,5-imidazolidinedione. The spraying solution also contained 3.5% glycerol and 175 ppm of an alkyl polyethylene oxide surface-active agent (Tergitol® 15-S-12). Two other plants were sprayed with glycerol-surface active agent solution without the compound and an additional plant was not sprayed.

On the following day, these plants were exposed to 75 pphm $O_3$ for 2.5 hours in a fumigation chamber having about one air change a minute. Two days later, the plants were examined. The ozone had caused extensive damage to the two primary leaves of the unprotected plants. Damage consisted of brown lesions and bifacial tissue collapse. In the unsprayed plant, the damage area made up 90% of the leaf area. The plants sprayed with glycerol and surface active agent only were damaged to the extent of over 50% of the leaf surface. The protected plant suffered no visible damage. This plant was returned to ozone (66 pphm) for 2.5 hours. When the plant was examined two days later, there was still no visible damage. A fresh unsprayed control plant, which was fumigated with the test plant, was damaged to the extent of 55% of its leaf area.

EXAMPLE VII

Conditions employed were similar to Example VI except the test plant was sprayed with a 500 ppm solution of 1,3-dimethyl-4-(2-fluorophenylureido)-2,5-imidazolidinedione. Two days after fumigation, the foliar damage was 0%. The plant was refumigated. Two days later, the damage was only 15%.

EXAMPLE VIII

The general procedure of Example VI was repeated except the test plant was sprayed with a 500 ppm solution of 1,3-dimethyl-4-(4-fluorophenylureido)-2,5-imidazolidinedione. Two days after fumigation with ozone, no damage was visible. The plant was fumigated a second time. Two days later, there was still no observable foliar damage. An unsprayed control plant was damaged to the extent of 45% by the first fumigation and 80% by the second.

EXAMPLE IX

The general procedure of Example VI was repeated except the test plant was sprayed with a 500 ppm solution of 1,3-dimethyl-4-(4-methoxyphenylureido)-2,5-imidazolidinedione. Two days after fumigating with ozone, only 5% visible damage was found. The plant was fumigated again and examined two days later. There was no additional damage.

EXAMPLE X

Pinto beans were grown in sand contained in 4-inch pots. Two 14-day old plants were treated by adding 20 ml of a 200 ppm solution of 1,3-dimethyl-4-(phenylureido)-2,5-imidazolidineodine to each pot. On the following day, these plants along with two control plants were fumigated 2.5 hours with 80 pphm ozone. Two days later, the treated plants had 0 and 5% foliar damage, respectively, whereas the controls had 80 and 95% respectively. The treated plants were fumigated again. Two days later, the damage was observed to be only 5 and 10% respectively.

As mentioned, the method of application to inhibit ozone damage of plant foliage can vary. Preferably, the compounds are applied as a foliar spray in aqueous media at a concentration of about 500 ppm. However, compounds of Examples VI and VII give good protection when applied at concentrations of 50 ppm. For foliar applications, it is preferred that a conventional wetting agent be present, e.g. 50–500 ppm of a nonionic detergent to aid in uniform coverage.

In place of foliar application, the compounds can be applied to soil for absorption through the roots. The latter may provide effectiveness over a greater length of time than generally effective as a foliar spray. Foliar applications are preferred to be within a week before exposure to atmosphere containing a substantial amount of ozone.

I claim:

1. A method of protecting plants against damage caused by ozone consisting essentially of applying, to the plants to be protected, an effective amount of a compound of the formula:

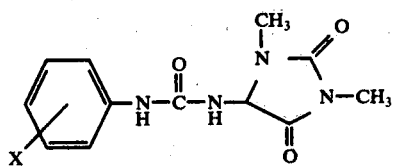

wherein X is selected from hydrogen, fluorine, methoxy, meta-chlorine, or meta-bromine;

and at least one (a) inert diluent or (b) surfactant, and wherein said plants are selected from pinto bean, orange, lemon, tobacco, grape, potato, tomato, soybean, corn, lettuce, and alfalfa plants.

2. The method of claim 1 wherein X is selected from hydrogen, fluorine, or para-methoxy.

3. The method of claim 1 wherein X is hydrogen.

4. The method of claim 1 where X is para-fluorine.

5. The method of claim 1 wherein X is ortho-fluorine.

6. The method of claim 1 wherein X is para-methoxy.